United States Patent [19]

Spector

[11] Patent Number: 4,824,707
[45] Date of Patent: Apr. 25, 1989

[54] DECORATIVE AIR FRESHENER UNIT

[76] Inventor: Donald Spector, 380 Mountain Rd., Union City, N.J. 07087

[21] Appl. No.: 211,702

[22] Filed: Jun. 27, 1988

[51] Int. Cl.$^4$ ............................ B32B 3/14; B44C 1/28
[52] U.S. Cl. ........................................ 428/46; 239/35; 428/49; 428/905
[58] Field of Search ............................ 428/46, 49, 905; 239/35

[56] References Cited

U.S. PATENT DOCUMENTS

| | | | |
|---|---|---|---|
| 4,243,224 | 1/1981 | Spector | 428/905 X |
| 4,419,396 | 12/1983 | Sugimoto | 428/905 X |
| 4,528,226 | 7/1985 | Sweeny | 428/905 X |
| 4,606,956 | 8/1986 | Charbonneau et al. | 428/905 X |
| 4,687,203 | 8/1987 | Spector | 428/905 X |
| 4,696,844 | 9/1987 | Spector | 428/905 X |
| 4,720,409 | 1/1988 | Spector | 428/905 X |

*Primary Examiner*—Henry F. Epstein
*Attorney, Agent, or Firm*—Michael Ebert

[57] ABSTRACT

An air freshener unit having an impermeable backing sheet that is adherable to a substrate, and a facing sheet laminated to the backing sheet. Trapped between the sheets is a rupturable capsule containing a supply of a volatile fragrance. The facing sheet is formed of microporous, opaque material having good wicking properties. Printed on the rear surface of the facing sheet or on the front surface of the backing sheet is artwork that is normally blocked from view; but when the unit is activated by rupturing the capsule, the released fragrance is absorbed and exuded by the facing sheet which is made wet thereby and rendered translucent. As a result, the artwork becomes visible to a viewer. But when the exuded fragrance approaches exhaustion, the facing sheet, as it dries, reverts to its normal opacity, thereby causing the artwork to fade from view to signal to a user the need for a fresh unit.

11 Claims, 1 Drawing Sheet

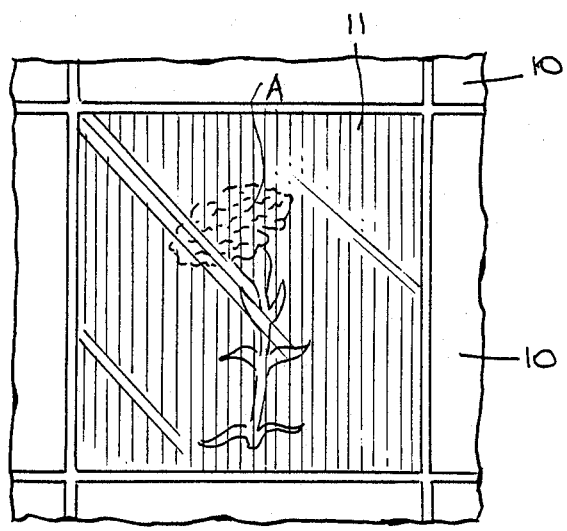
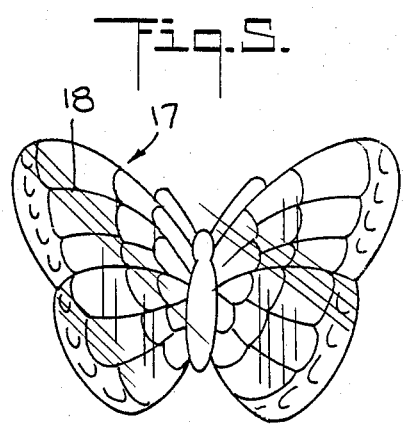
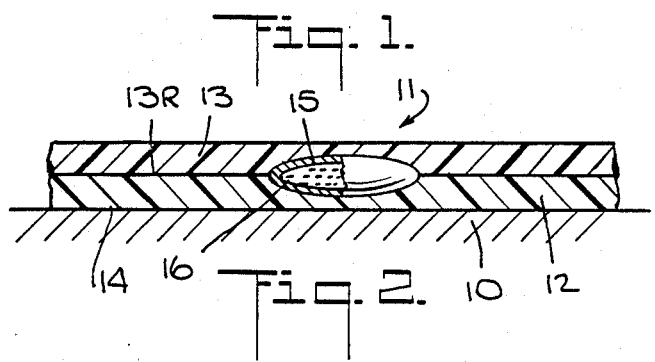
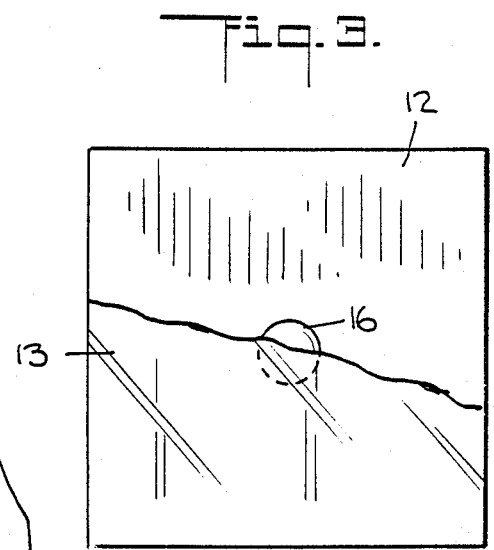
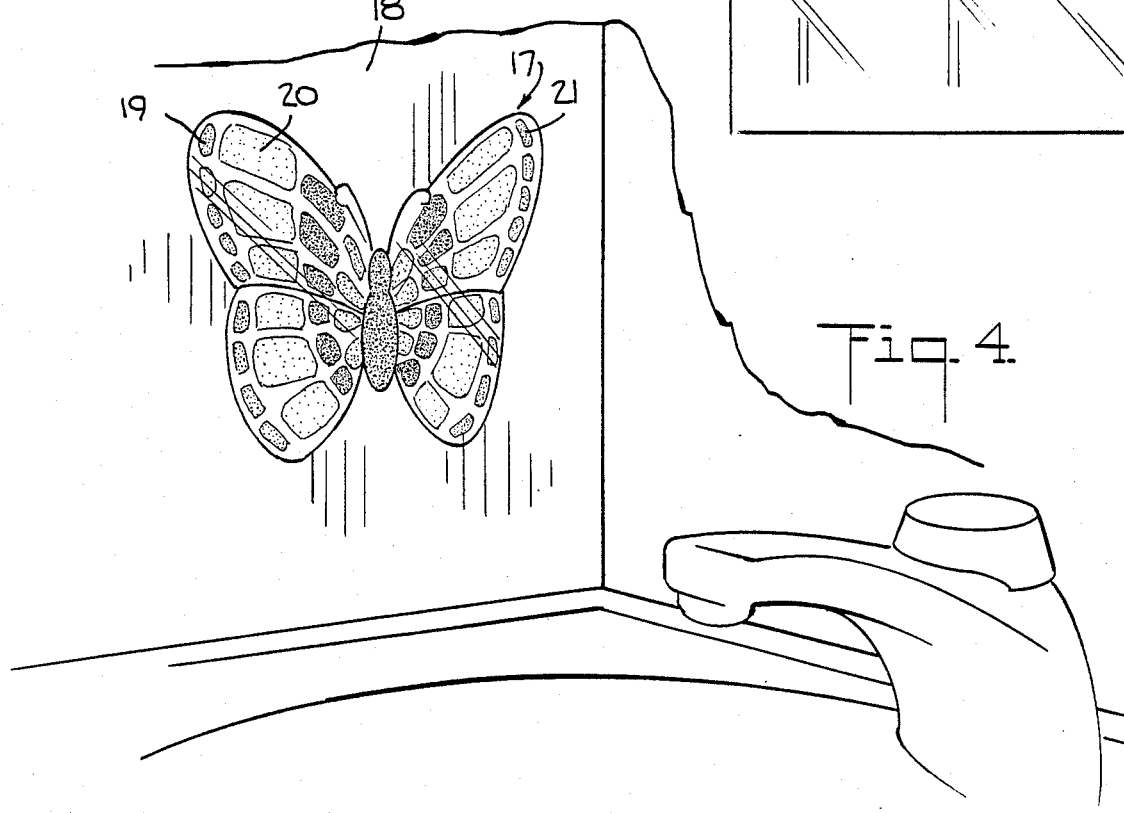

DECORATIVE AIR FRESHENER UNIT

BACKGROUND OF INVENTION

1. Field of Invention

This invention relates generally to air fresheners which release an aroma into the atmosphere of a room or other enclosure, and more particularly to a decorative air freshener unit that is adherable to tile or other flat substrate to render an interior atmosphere more pleasing, the unit indicating when its fragrance is exhausted.

2. Status of Prior Art

As used herein, the term "aroma" or "fragrance" is not limited to perfume-like odors, but encompasses any odor that is suitable as an air freshener to condition, modify or otherwise charge the ambient atmosphere.

The aroma of perfumes and perfume-based products such as colognes and toilet waters was originally derived from the essential oil of plants. However, since the early 19th century, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents, the ingredients are combined with a highly volatile alcohol carrier.

The concern of the present invention is with a decorative air freshener unit that can be adhered to a tile, a wall or any other substrate to render the atmosphere of a room or other enclosure more pleasing.

My prior 1988 U.S. Pat. No. 4,720,409 discloses an air freshener of the film laminate type which is adherable to a wall tile in a bathroom or kitchen or to any other flat substrate such as a window. This film laminate includes a transparent, plastic face film impregnated with a volatile fragrance that is slowly released from the film. The concentration of the fragrance in the film is such as to result in prolonged emission. The face film is laminated to a transparent backing film in a manner which does not impair the transparency of the laminate.

Imprinted on the front surface of the backing film is artwork representing an aroma-producing object of some sort. This artwork is effectively sandwiched between the face film and the backing film and is thereby protected. The rear surface of the backing film is coated with a low tack, pressure-sensitive adhesive. Thus, the laminate may be adhered onto a smooth tile or window and later pulled therefrom when the fragrance is exhausted.

The problem encountered with an air freshener unit of the type disclosed in my prior patent as well as other forms of air fresheners having a limited supply of fragrance is that the user is unable to tell just when the supply is exhausted and the unit is no longer effective. The reason for this inability is that an exhausted unit has a residual odor that lingers on well after the unit has run out of fragrance.

SUMMARY OF INVENTION

In view of the foregoing, the main object of this invention is to provide a replaceable air freshener unit which is adherable onto a wall or other substrate to exude, when activated, a pleasing fragrance into the atmosphere, which unit when the supply of fragrance approaches exhaustion, indicates this condition.

A significant advantage of this invention is that it not only makes it possible for the user to know when the replace the unit, but it also affords the seller of the unit greater sales; for informed users will be induced to purchase fresh units.

More specifically, an object of this invention is to provide a unit of the above type which when activated exhibits an artwork which remains visible until the unit approaches exhaustion, at which point it fades out to signal the exhausted condition of the unit.

Also an object of this invention is to provide an air freshener unit that may be mass produced at low cost and which operates efficiently and reliably.

Briefly stated, these objects are attained in an air freshener unit having an impermeable backing sheet that is adherable to a substrate, and a facing sheet laminated to the backing sheet. Trapped between the sheets is a rupturable capsule containing a supply of a volatile fragrance. The facing sheet is formed of microporous, opaque material having good wicking properties. Printed on the rear surface of the facing sheet or on the front surface of the backing sheet is artwork that is normally blocked from view; but when the unit is activated by rupturing the capsule, the released fragrance is absorbed and exuded by the facing sheet which is made wet thereby and rendered translucent. As a result, the artwork becomes visible to a viewer. But when the exuded fragrance approaches exhaustion, the facing sheet, as it dries, reverts to its normal opacity, thereby causing the artwork to fade from view to signal to a user the need for a fresh unit.

BRIEF DESCRIPTION OF DRAWINGS

For a better understanding of the invention as well as other objects and further features thereof, reference is made to the following detailed description to be read in conjunction with the accompanying drawings, wherein:

FIG. 1 shows a decorative air freshener unit in accordance with the invention in a square format adhered to a wall tile;

FIG. 2 is a section taken through the unit;

FIG. 3 is a plan view of the unit, with the facing sheet torn away to expose the underlying backing sheet and the fragrance capsule;

FIG. 4 shows an air freshener unit in a contoured format adhered to a glass panel, the unit having the configuration of a butterfly; and FIG. 5 shows the FIG. 4 unit after its supply of fragrance is exhausted.

DETAILED DESCRIPTION OF INVENTION

First Embodiment:

Referring now to FIGS. 1, 2 and 3, there is shown a tiled wall composed of a uniform array of like ceramic or composition tiles 10 having a smooth or glazed surface. A wall of this type is conventional in a kitchen, a bathroom or other enclosure subject to unpleasant odors. The tiles are of solid color (i.e., white, green or blue). In this tiled environment, the need exists for an air freshener unit to render the atmosphere more pleasing or to at least mask the prevailing odors.

Adhered to a selected tile is an air freshener unit according to the invention in a square format that matches the dimensions of the tile. The unit, generally designated by numeral 11, is formed by a laminate constituted by an impermeable base or backing sheet 12 laminated to a microporous facing sheet 13. Backing sheet 12 in this embodiment is formed of transparent, flexible, synthetic plastic film material such as "Mylar" (polyester), or an impermeable, clear film having similar properties.

The rear surface of sheet 12 is coated with a clear, low-tack, pressure-sensitive adhesive layer 14. Suitable for this purpose is the low-tack adhesive used by 3M on its well known "Post-Em" sheets. Hence, it is an easy matter to adhere the unit to a tile (or other flat substrate) and to peel off the unit when it is exhausted, and to replace it with a fresh unit.

Facing sheet 13, which is edge-laminated by heat and pressure or by other means to backing sheet 12, is made of a printable, microporous material having good wicking properties that is normally opaque but is rendered translucent when wetted by a liquid. Suitable for this purpose is TESLIN, a synthetic plastic printing sheet material manufactured and sold by PPG (Pittsburgh Plate Glass Industries—Barbertown, Ohio).

TESLIN is a single layer, totally synthetic, microporous, polyethylene sheet having silica dispersed therein. When dry, this material has an opacity of 88% and a bright white or off-white color. Because of its exceptionally smooth and uniform surface, TESLIN is excellent for printing or lamination. Despite its microporous structure, its physical properties are unaffected by water or liquid fragrances, and it will not break down or delaminate. It is chemically inert to standard liquid fragrances and has good resistance to degradation by sunlight or radiation from fluorescent lamps.

A TESLIN sheet can be printed by conventional processes, such as offset, gravure or by screen techniques. Its uniform surface affords good resolution when TESLIN is printed with conventional or specialty printing inks. When the impressed ink images are dry, they are permanently bonded to the TESLIN surface.

Because of its wicking properties, when TESLIN is made wet in a given area with a volatile liquid fragrance, the fragrance will be wicked thereby throughout the sheet and will impregnate the myriad pores thereof. And because the fragrance is in a volatile alcohol carrier, its scent will be exuded from the entire surface of the sheet. The optical properties of TESLIN are such that when impregnated with liquid fragrance, the sheet will lose its opacity and be rendered translucent. But when the liquid fragrance is exhausted and the sheet is again dry, it will recover its normal opacity.

Entrapped between facing sheet 13 and backing sheet 12 is a small rupturable capsule 15 containing a supply 16 of liquid fragrance. Capsule 15 is formed of gelatine or other material that is easily ruptured by an applied pressure, so that when the capsule is ruptured, the released liquid fragrance soaks into the facing sheet and is gradually exuded therefrom to discharge the fragrance into the atmosphere. However, it is not absorbed by the impermeable Mylar backing sheet 12.

Printed on the rear surface 13R of facing sheet 13 is artwork A, such as a flower whose natural aroma matches the fragrance impregnating the sheet. Hence, one viewing this printed flower also in effect smells it.

However, artwork A, because it is printed on the rear surface of a normally opaque sheet, is not visible to a viewer until the air freshener is activated by rupturing capsule 15; for in doing so, the sheet is rendered translucent. In due course, depending on the limited supply of fragrance, the fragrance exuded from the air freshener unit approaches exhaustion. And as sheet 13 then proceeds to dry, it gradually recovers its normal opacity, and in doing so, the artwork begins to fade from view and altogether disappears when the sheet is completely dry.

Thus, when the air freshener is first installed on a substrate, the artwork is not seen until the capsule is ruptured. And as soon as the sheet is made wet by the liquid fragrance, the artwork becomes fully visible and remains visible until such time as the fragrance approaches exhaustion. In this way, the user of the air freshener unit is given a signal indicative of approaching exhaustion of the unit and the need to replace it with a fresh unit.

In practice, instead of a rupturable capsule, the liquid fragrance may be encapsulated in a weak wall film material such as BAREX which is sandwiched between the facing sheet and the backing sheet, so that by bending or twisting the unit, the weak film is ruptured to release the fragrance. Or the microporous sheet may be factory-impregnated with the liquid fragrance and covered by a peel-off sealing film, so that the unit is activated by removing the sealing film.

Second Embodiment:

In the embodiment shown in FIGS. 4 and 5, an air freshener unit, generally designated by numeral 17, is adhered to a glass panel 18 of a bathroom. This unit is contoured to assume the form of a butterfly.

In this instance, the front surface of the microporous facing sheet is printed in black ink, as shown in FIG. 5, so as to outline the wing structure of the butterfly. The rear surface of the normally-opaque facing sheet is printed in multiple colors which lie within the outline of the wings to impart colors 19, 20 and 21 thereto. But these colors which appear only in FIG. 4 are not visible until the unit is activated and in the microporous sheet is made wet and rendered translucent.

Thus, in the activated condition of the unit, as shown in FIG. 4, the viewer sees a highly colored butterfly. But when the supply of liquid fragrance approaches exhaustion and the facing sheet proceeds to dry, the colors fade out until all that remains visible is the outline of the butterfly wings, this signalling that the unit is exhausted and must be replaced with a fresh unit.

Instead of a blank exhausted freshener unit as in the first embodiment, the unit in the second embodiment initially shows the outline of a form. But when the unit is activated, it becomes highly colored and reverts to the outline form only when the unit is exhausted. The butterfly configuration is by way of example only, and in practice, many other contoured figurative forms may be used.

While there have been shown and described preferred embodiments of a decorative air freshener unit in accordance with the invention, it will be appreciated that many changes and modifications may be made therein without, however, departing from the essential spirit thereof. Thus, instead of printing artwork on the rear surface of the facing sheet, it may be printed on the front surface of the backing sheet.

The reason a normally opaque material such as TESLIN or other highly porous polyethylene based materials are rendered translucent when impregnated with an oil-based fragrance liquid, is that these materials, though hydrophobic, have an altogether different characteristic in regard to liquid lipids. And while they reject water, they have a strong affinity for lipids and are therefore lipophilic or oleophilic. The optical properties or refraction index of oil is such to produce translucency, just as paper which is opaque when dry becomes translucent when oiled.

I claim:

1. An air freshener unit adherable to a flat substrate to exude a fragrance into the atmosphere from a limited supply and to signal when the supply of fragrance approaches exhaustion, said unit comprising:
   (A) an impermeable backing sheet whose rear surface is adherable to the substrate;
   (B) a facing sheet laminated to the backing sheet and formed of normally opaque microporous material having an affinity for liquid lipids and which becomes translucent when wet by liquid lipids, the rear surface of the facing sheet or the front surface of the backing sheet having artwork printed thereon which is normally blocked from view by the opacity of the facing sheet; and
   (C) a rupturable supply of volatile oil-based liquid fragrance interposed between the sheets, the unit being activated by rupturing the supply to release the liquid fragrance and cause it to impregnate the pores of the facing sheet and to be exuded therefrom, the facing sheet being rendered translucent by the oil in the liquid fragrance impregnated therein to render the artwork visible until such time as the liquid fragrance approaches exhaustion and the facing sheet dries to again block the artwork from view.

2. A unit as set forth in claim 1, wherein the rear surface of the backing sheet is coated with a low-tack, pressure-sensitive adhesive.

3. A unit as set forth in claim 1, wherein the backing sheet is formed of transparent polyester film.

4. A unit as set forth in claim 1, wherein the facing sheet is formed of microporous polyethylene material having silica dispersed therein.

5. A unit as set forth in claim 1, wherein said supply is encapsulated in a gelatin capsule.

6. A unit as set forth in claim 1, wherein said unit is in a square format adherable to a tile of about the same dimensions.

7. A unit as set forth in claim 1, wherein said unit is in a contoured figurative form.

8. A unit as set forth in claim 7, wherein said form is that of a butterfly and said facing sheet has imprinted on its front surface the outline of the wings of a butterfly.

9. A unit as set forth in claim 7, wherein imprinted on the rear surface of the facing sheet are the multiple colors of the wings which are visible only when the facing sheet is wet.

10. A unit as set forth in claim 1, wherein said fragrance is an oil-based fragrance in a volatile alcohol carrier.

11. An air freshener unit adapted to exude an oil-based fragrance into the atmosphere from a limited supply thereof and to signal when the supply of fragrance approaches exhaustion, said unit comprising:
    (A) an impermeable backing sheet; and
    (B) a facing sheet laminated to the backing sheet and formed of normally opaque microporous material having an affinity for liquid lipids and which becomes translucent when wetted with said oil-based fragrance, the rear surface of the facing sheet or the front surface of the backing sheet having artwork printed thereon which is normally blocked from view by the opacity of the facing sheet, whereby when the facing sheet is made translucent by the liquid fragrance, this renders the artwork visible until such time as the liquid fragrance approaches exhaustion and the facing sheet dries to again block the artwork from view.

* * * * *